US010478330B2

(12) United States Patent
Wiltshire et al.

(10) Patent No.: US 10,478,330 B2
(45) Date of Patent: Nov. 19, 2019

(54) OSTOMY APPLIANCE

(71) Applicant: Salts Healthcare Limited, Birmingham, West Midlands (GB)

(72) Inventors: Neil Wiltshire, West Midlands (GB); Peter Argent, West Midlands (GB)

(73) Assignee: Salts Healthcare Limited, Birmingham, West Midlands (GB)

(*) Notice: Subject to any disclaimer, the term of this patent is extended or adjusted under 35 U.S.C. 154(b) by 919 days.

(21) Appl. No.: 14/780,246

(22) PCT Filed: Mar. 14, 2014

(86) PCT No.: PCT/GB2014/050823
§ 371 (c)(1),
(2) Date: Sep. 25, 2015

(87) PCT Pub. No.: WO2014/162109
PCT Pub. Date: Oct. 9, 2014

(65) Prior Publication Data
US 2016/0058604 A1    Mar. 3, 2016

(30) Foreign Application Priority Data

Apr. 5, 2013 (GB) .................................. 1306189.0

(51) Int. Cl.
*A61F 5/445* (2006.01)
*A61F 5/44* (2006.01)
*A61F 5/441* (2006.01)

(52) U.S. Cl.
CPC .............. *A61F 5/445* (2013.01); *A61F 5/441* (2013.01); *A61F 5/4404* (2013.01); *A61F 5/4405* (2013.01)

(58) Field of Classification Search
CPC combination set(s) only.
See application file for complete search history.

(56) References Cited

U.S. PATENT DOCUMENTS 4,084,590 A * 4/1978 Caraway ................. A61F 5/445
604/335
4,411,659 A * 10/1983 Jensen .................... A61F 5/441
604/332

(Continued)

FOREIGN PATENT DOCUMENTS

EP    0443728    8/1991
EP    1022002    7/2000

(Continued)

*Primary Examiner* — Tatyana Zalukaeva
*Assistant Examiner* — Guy K Townsend
(74) *Attorney, Agent, or Firm* — Boyle Fredrickson, S.C.

(57) ABSTRACT

An ostomy appliance having:—
 first and fourth walls connected to each other at or near their peripheries, the first wall having a stoma-receiving opening;
 second and third walls positioned in between the first and fourth walls, the second wall being connected to one or more of the first, third and/or fourth walls, and the third wall being connected to one or more of the first, second and/or fourth walls;
 a waste collecting cavity defined between either the first and second walls or first and fourth walls;
 a second cavity defined between the second and third walls;
 a third cavity defined between the third and fourth walls;
 a first gas flow path in the second wall to permit waste gases to pass from the waste collecting cavity to the second cavity;
 a second gas flow path in the third wall to permit waste gases to pass from the second cavity to the third cavity; and
 a third gas flow path in the fourth wall to permit waste gases to escape from the third cavity, (Continued)

wherein the second and third walls are connected to each other so as to define a liquid flow path which permits liquid within the second cavity to flow into the waste collecting cavity.

19 Claims, 8 Drawing Sheets

(56) References Cited

U.S. PATENT DOCUMENTS

| | | | | |
|---|---|---|---|---|
| 4,519,797 | A * | 5/1985 | Hall | A61F 5/445 604/332 |
| 4,604,095 | A * | 8/1986 | Samuelsen | A61F 5/4405 604/323 |
| 4,826,495 | A * | 5/1989 | Petersen | A61F 5/441 604/333 |
| 4,917,689 | A * | 4/1990 | Coombes | A61F 5/445 604/338 |
| 5,009,648 | A * | 4/1991 | Aronoff | A61F 5/445 604/332 |
| 5,250,042 | A * | 10/1993 | Torgalkar | A61F 5/441 604/333 |
| 5,468,235 | A * | 11/1995 | La Gro | A61F 5/441 604/333 |
| 5,549,587 | A * | 8/1996 | Norton | A61F 5/441 604/333 |
| 5,591,144 | A * | 1/1997 | Smith | A61F 5/445 604/327 |
| 5,690,622 | A * | 11/1997 | Smith | A61F 5/441 128/DIG. 24 |
| 5,690,623 | A * | 11/1997 | Lenz | A61F 5/441 604/332 |
| 5,865,819 | A * | 2/1999 | Cisko, Jr. | A61F 5/445 604/327 |
| 6,171,288 | B1 * | 1/2001 | Wiltshire | A61F 5/441 604/333 |
| 6,506,184 | B1 * | 1/2003 | Villefrance | A61F 5/441 604/333 |
| 6,659,988 | B1 * | 12/2003 | Steer | A61F 5/441 604/333 |
| 6,709,421 | B1 * | 3/2004 | Falconer | A61F 5/441 604/335 |
| 6,773,420 | B2 * | 8/2004 | Kanbara | A61F 5/441 604/333 |
| 7,476,220 | B2 * | 1/2009 | Lillegaard | A61F 5/4404 4/144.2 |
| 9,119,727 | B2 * | 9/2015 | Hannan | A61F 5/4405 |
| 9,549,839 | B2 * | 1/2017 | Schertiger | A61F 5/441 |
| 9,962,282 | B2 * | 5/2018 | Chang | A61F 5/445 |
| 2003/0014023 | A1 * | 1/2003 | Kanbara | A61F 5/441 604/333 |
| 2004/0059306 | A1 * | 3/2004 | Tsal | A61F 5/4404 604/332 |
| 2009/0163883 | A1 * | 6/2009 | Christensen | A61F 5/4405 604/328 |
| 2010/0010460 | A1 * | 1/2010 | Butler | A61F 5/441 604/333 |
| 2010/0145291 | A1 * | 6/2010 | Kambara | A61F 5/441 604/333 |
| 2011/0196323 | A1 * | 8/2011 | Gill | A61F 5/4405 604/333 |
| 2012/0283678 | A1 * | 11/2012 | Nguyen-DeMary | A61F 5/445 604/337 |
| 2014/0194843 | A1 * | 7/2014 | Masters | A61F 5/4405 604/333 |
| 2015/0320585 | A1 * | 11/2015 | Fattman | A61F 5/445 604/344 |

FOREIGN PATENT DOCUMENTS

| | | | | |
|---|---|---|---|---|
| EP | 1022002 A1 | * | 7/2000 | A61F 5/441 |
| EP | 1022002 A1 | * | 7/2000 | A61F 5/441 |
| GB | 2149306 | | 6/1985 | |
| GB | 2149306 A | * | 6/1985 | A61F 5/441 |
| GB | 2345853 | | 7/2000 | |
| GB | 2413083 | | 10/2005 | |
| GB | 2484978 | | 5/2012 | |
| GB | 2484978 A | * | 5/2012 | A61F 5/441 |

* cited by examiner

OSTOMY APPLIANCE

DESCRIPTION OF INVENTION

The invention relates to an ostomy appliance for collecting human waste. It should be understood that the invention can be utilised in drainable and non-drainable ostomy appliances. The invention is applicable to both one piece and two piece ostomy appliances.

According to a first aspect of the invention, we provide an ostomy appliance having:—
- first and fourth walls connected to each other at or near their peripheries, the first wall having a stoma-receiving opening;
- second and third walls positioned in between the first and fourth walls, the second wall being connected to one or more of the first, third and/or fourth walls, and the third wall being connected to one or more of the first, second and/or fourth walls;
- a waste collecting cavity defined between either the first and second walls or first and fourth walls;
- a second cavity defined between the second and third walls;
- a third cavity defined between the third and fourth walls;
- a first gas flow path in the second wall to permit waste gases to pass from the waste collecting cavity to the second cavity;
- a second gas flow path in the third wall to permit waste gases to pass from the second cavity to the third cavity; and
- a third gas flow path in the fourth wall to permit waste gases to escape from the third cavity,
- wherein the second and third walls are connected to each other so as to define a liquid flow path which permits liquid within the second cavity to flow into the waste collecting cavity.

According to a second aspect of the invention, we provide an ostomy appliance having:—
- first and fourth walls connected to each other at or near their peripheries, the first wall having a stoma-receiving opening;
- a second wall positioned in between the first and fourth walls, the second wall being connected to one or more of the first and/or fourth walls;
- a waste collecting cavity defined between either the first and second walls or first and fourth walls;
- a second cavity defined between the second and fourth walls;
- a first gas flow path in the second wall to permit waste gases to pass from the waste collecting cavity to the second cavity; and
- a gas flow path in the fourth wall to permit waste gases to escape from the second cavity;
- wherein the second and fourth walls are connected to each other so as to define a liquid flow path which permits liquid within the second cavity to flow into the waste collecting cavity.

Further features of the first and second aspect of the invention are set out in claims 2 to 18 appended hereto.

Embodiments of the invention will now be described by way of example only with reference to the accompanying drawings, of which:—

Figure 1:
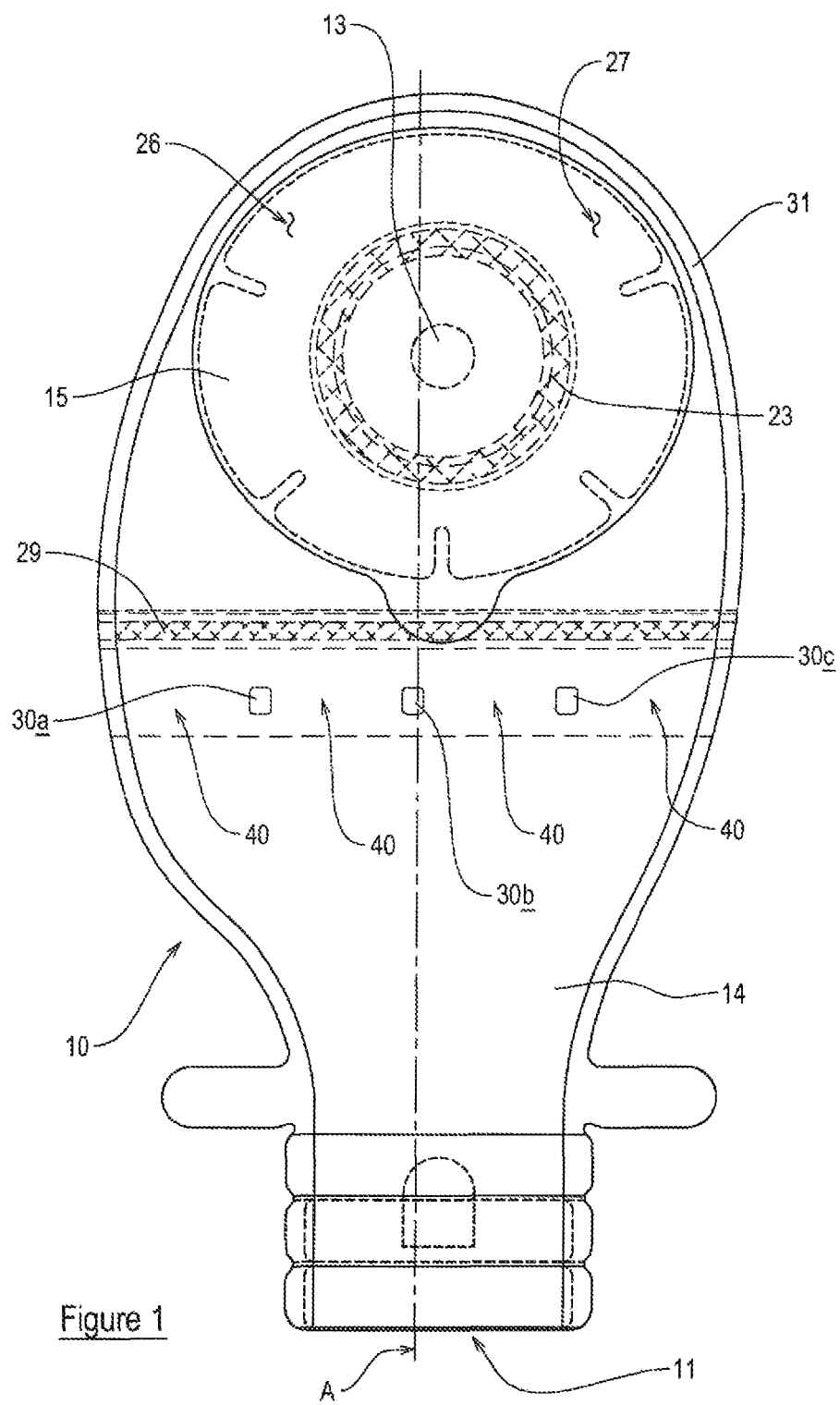
FIG. 1 is a front view of a first embodiment of an apparatus according to the present invention.
Figure 2:
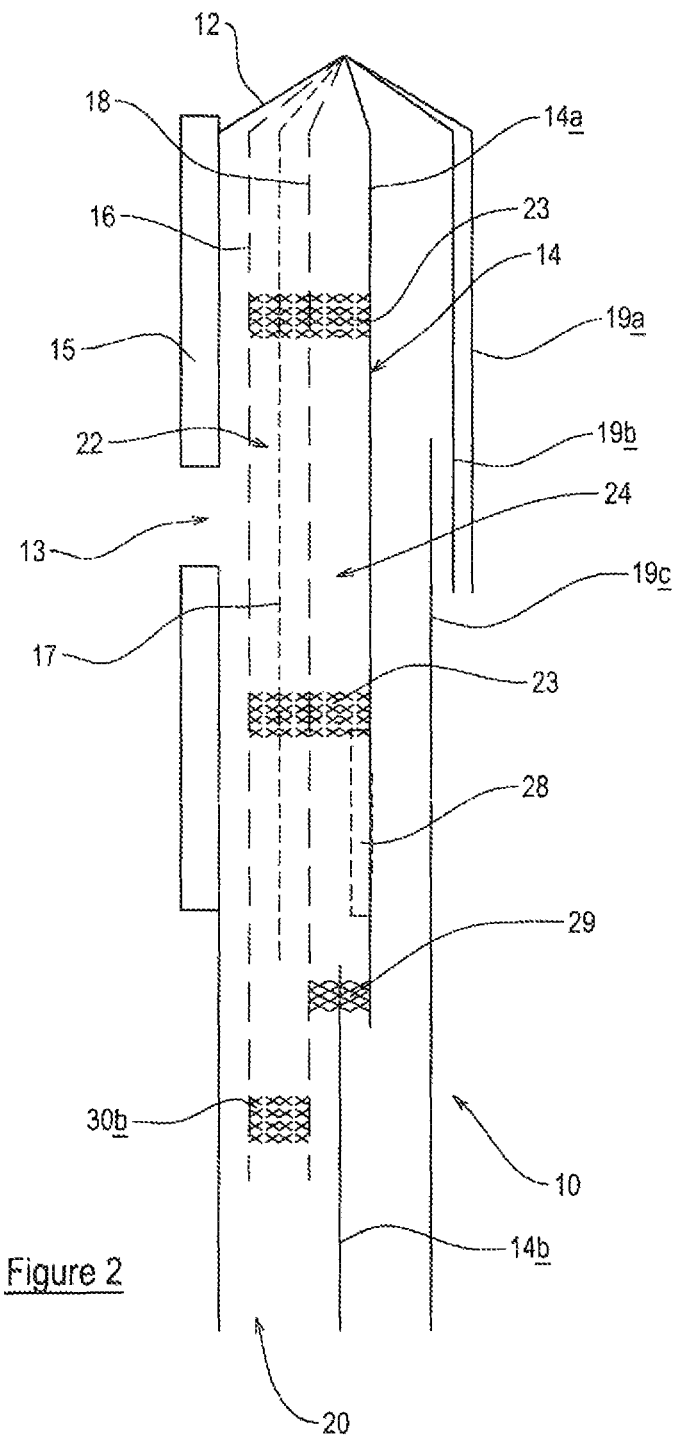
FIG. 2 is a cross-sectional view of the apparatus of FIG. 1 through the line A.

Referring firstly to FIGS. 1 and 2 these show a first embodiment of an ostomy appliance in accordance with the present invention, shown generally at 10. The general construction of the ostomy appliance 10 is similar to those well known in the art and in that sense it includes a pair of outermost walls, first 12 and fourth 14, which are connected to each other at or near their peripheries, for example by heat welding or using an adhesive. The ostomy appliance shown is a drainable appliance, meaning that its contents can be emptied through an opening 11 between the walls 12, 14. The wall 14 is provided as first 14a and second 14b portions which are connected to each other along a lateral weld line 29.

The first wall 12 has a stoma-receiving opening 13 and is connected to a generally circular flange 15 which is manufactured from a hydrocolloid material, for adhering the appliance 10 to a user around their stoma.

The ostomy appliance 10 in the present embodiment includes second 16 and third 18 walls which are positioned in between the first 12 and fourth 14 walls (see FIG. 2). In this embodiment the second 16 and third 18 walls are connected to both of the first 12 and fourth 14 walls by a common peripheral weld 31. The third wall 18 is also connected to the wall 14b by the common weld 29. It should be appreciated, however, that in alternative embodiments the second wall 16 could be connected to one or more of the first 12, third 18 and/or fourth 14 walls at or near their peripheries. It should also be appreciate that an alternative embodiments the third wall 18 may instead by connected to one or more of the first 12, second 16 and/or fourth 14 walls at or near their peripheries. All that is necessary that the first, second, third and fourth walls are connected to each other, directly or indirectly so that their relative positions are maintained whilst the ostomy appliance 10 is being used.

The ostomy appliance 10, as can be seen from FIG. 2, defines a number of cavities therein. A waste collecting cavity 20 is provided which communicates with the opening 13 and at its lower end with an outlet 11. A majority of the waste collection cavity 20 is defined between the first 12 and second 16 walls, but the lowermost end, near the outlet 11, is defined by the first 12 and fourth 14 walls. The waste collecting cavity 20 is provided as the primary cavity for collecting a user's waste, which enters the cavity through the opening 13 in the wall 12.

A second cavity 22 is defined between the second 16 and third 18 walls. A third cavity 24 is defined between the third 18 and fourth 14 walls. The second 22 and third 24 cavities are not provided for waste storage, but rather provide a outlet therethrough to atmosphere for any waste gases. To provide this gas flow path the appliance 10 has a first gas flow path positioned in the second wall 16 in the form of a slit 26. A second gas flow path is provided in the third wall 18 also in the form of a slit 27. Finally a third gas flow path is provided in the fourth wall 14 in the form of an aperture 28 covered by a suitable gas filter. This combination of the first, second and third gas flow paths permits waste gases to escape from the waste collecting cavity 20 to atmosphere during use.

In accordance with the present invention the appliance 10 configured such that the second 16 and third 18 walls are connected to each other so as to define a liquid flow path 40 which permits any liquid within the second cavity 22 to flow into the waste collecting cavity 22. In the present embodiment it can be seen from FIG. 1 that the edges of the second 16 and third 18 walls which face the outlet 11 (those which are generally horizontal in normal use) are connected to each other by three heat welds 30a, 30b and 30c. These welds together with the peripheral weld 31 define four breaks, gaps or openings in the connection of the second 16 and third 18 walls to each other so as to provide four liquid flow paths 40. The liquid flow paths 40 are therefore configured to permit liquid to pass only in the direction of the second cavity to the waste collecting cavity, and in doing so, act as one-way valves. This is because the two walls 16, 18 will naturally part under the weight of any waste, to permit waste to pass from the cavity 22 and into the cavity 20, but will not generally easily part in the opposite direction, especially if there is already liquid between the walls. Any such liquid would help adhere the walls 16, 18 to each other so as to further prevent liquid flowing through the paths 40 and into the cavity 22.

Whilst it is not intended for any waste to flow from the waste collecting cavity 20 into the second cavity 22, it is sometimes the case that a small amount of waste flows through the slit 26 when, for example, a user lies down to sleep. Advantageously, any of the waste which does enter the second cavity 22 will flow, under gravity, into the waste collecting cavity 20 through the liquid flow paths 40 when the appliance is subsequently vertically aligned (e.g. when the user stands upright). Even if waste does flow into the second cavity 22 it is unlikely that any such waste will also flow into the third cavity 24, through the slit 27.

It can be seen that the appliance 10 includes a spacing wall 17 which is positioned in between the second 16 and third 18 walls. The purpose of this wall 17 is to act as a spacing material. It is preferably a porous material, so as to permit waste gases to pass through the cavity 22, but whilst preventing the walls 16 and 18 from sticking to each other should any waste pass from the cavity 20 and into the cavity 22.

Whilst in the above embodiment the first and second gas flow paths 26, 27 are provided as slits in the respective walls of the appliance 10, it should be appreciated that suitable apertures, which could also be covered by appropriate gas filters, could be used. Also, whilst the third gas flow path 28 is provided as an aperture in the wall 14, it could be a slit therein, and need not necessarily be covered by a gas filter.

It will seen from the figures that the second 16 and third 18 walls are smaller in surface area than first 12 and fourth 14 walls. This is so as to advantageously provide more space in a lower part of the appliance for waste to collect in the cavity 20. The walls 16 and 18 are therefore positioned in an upper portion of the appliance 10, generally opposite the stoma-receiving opening 13.

Whilst in the present embodiment there are four liquid flow paths 40, it should be appreciated that one, two, three or a greater number of liquid flow paths could be utilised. Also, whilst the liquid flow paths 40 are defined by breaks, gaps or openings between the heat welds 30a, 30b, 30c, it should be appreciated that any suitable connection could be provided between the second 16 and third 18 walls so as to provide at least one liquid flow path 40 therefrom and into the waste collecting cavity 20. For example, the second 16 and third 18 walls could be formed as a single sheet of material folded back on itself and there being a slit(s) or apertures(s) provided in or adjacent the fold so as to provide the liquid flow path(s) into the waste collecting cavity 20.

It will be seen on the figures that the appliance 10 includes a generally circular weld line 23 which connects the walls 16, 17, 18 and 14 to each other. This circumferential weld 23 defines therein a viewing port so that the user can view the opening 13. It will also be seen that the appliance 10 includes additional part-walls 19a, 19b, 19c. As is well known in the art, these walls are provided to increase user comfort. The walls 19a, 19b and 19c can be separated from one another so as to permit the user to look through the viewing port.

FIGS. 3 to 6 relate to second 10' (FIGS. 3 and 4) and third 10" (FIGS. 5 and 6) embodiments according to the present invention. Features which are in common with the first embodiment 10 have been given the same reference numeral with the addition of a single prime symbol for the second embodiment and a double prime symbol for the third embodiment.

Figure 3:
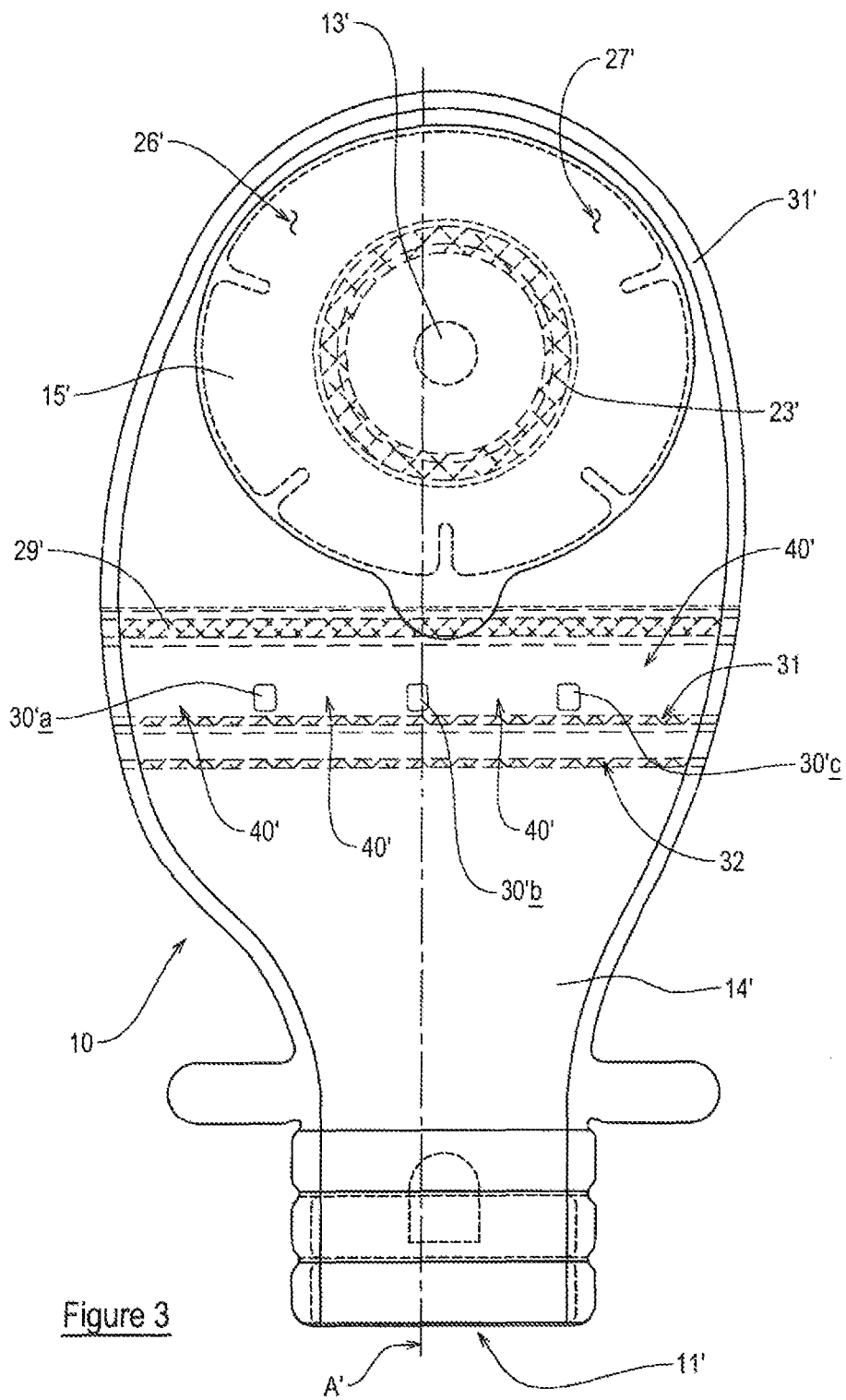
FIG. 3 is a front view of a second embodiment of an apparatus according to the present invention.
Figure 4:
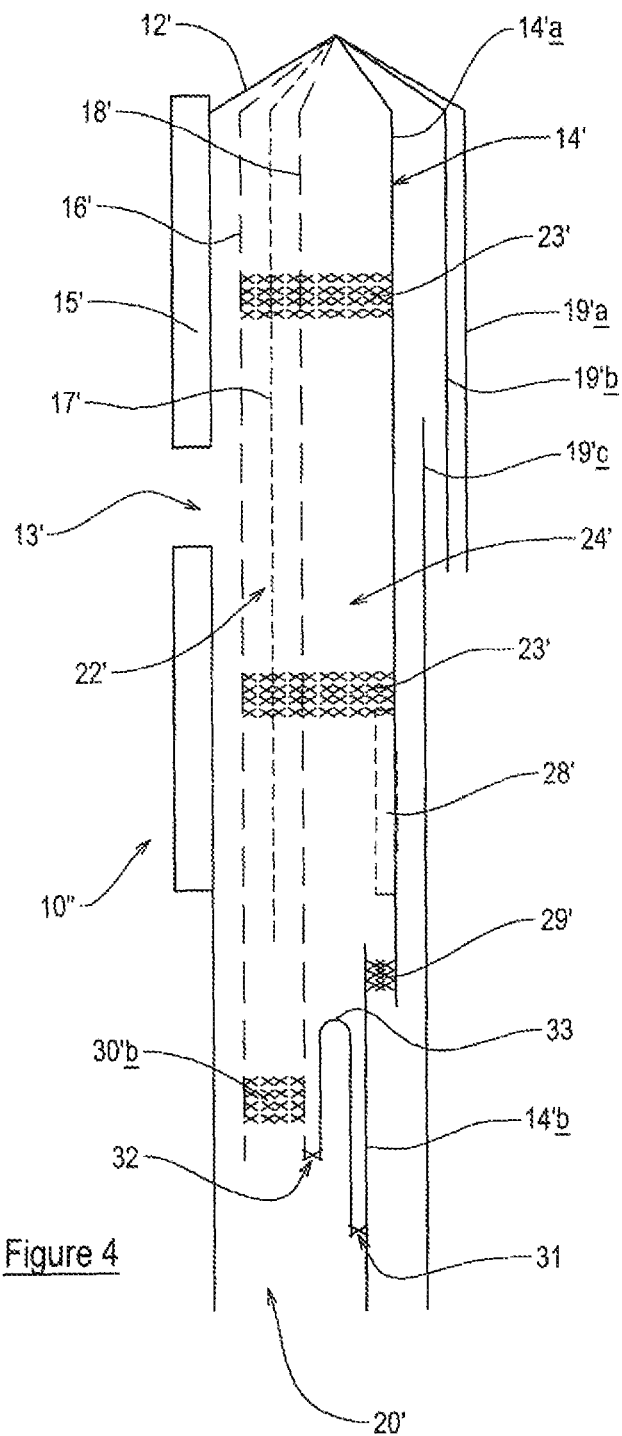
FIG. 4 is a cross-sectional view of the apparatus of FIG. 3 through the line A'.

Referring to FIGS. 3 and 4 the main difference is the connection of the third wall 18' to the fourth wall 14'. Instead of there being a direct weld, there is provided a further wall 33 which is connected along one edge 32 to a lower most edge of the wall 18' and along an opposite edge 31 to a lower most part of the wall 14'. In cross-section the wall 33 is n-shaped in the sense that it is a single wall which is folded back on itself. This additional wall 33 provides for increasing the available cavity space in the cavity 24' for waste gases before they exit through the aperture 28'.

Figure 5:
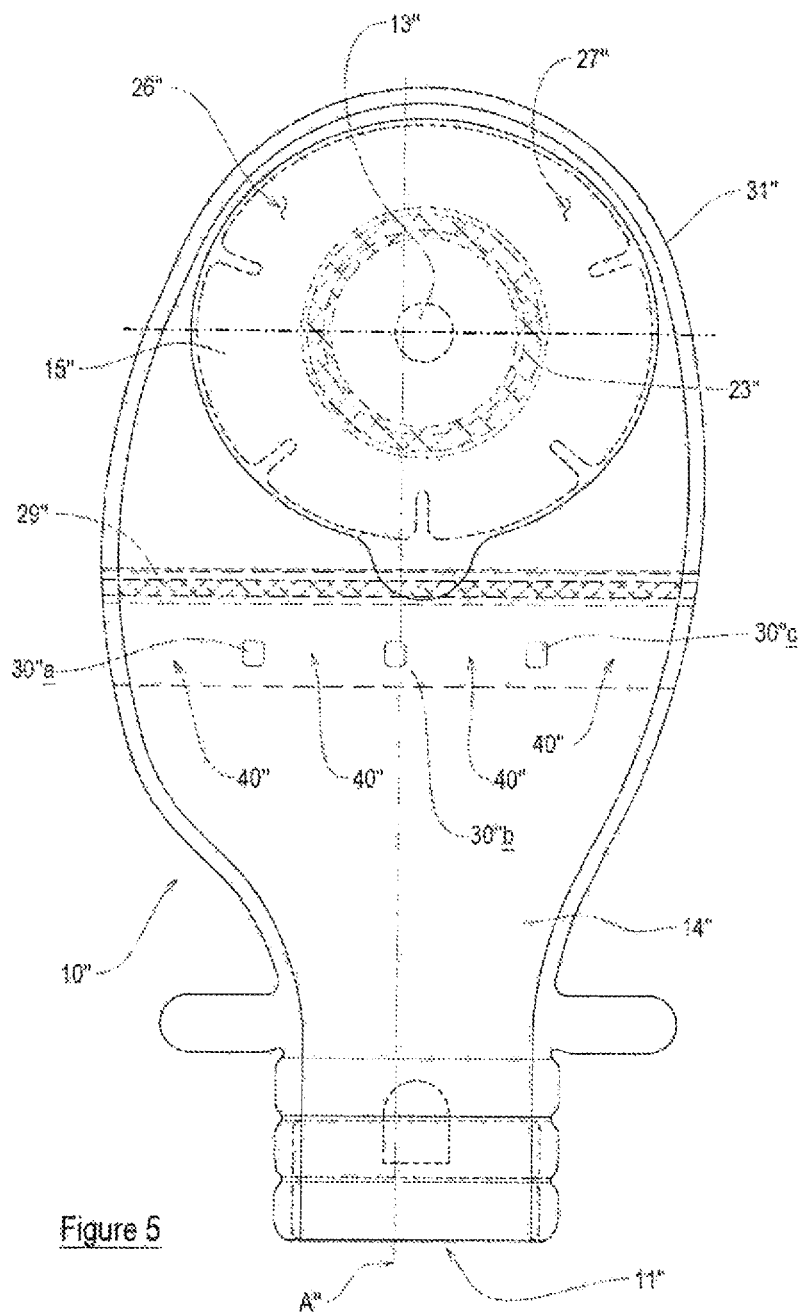
FIG. 5 is a front view of a third embodiment of an apparatus according to the present invention.
Figure 6:
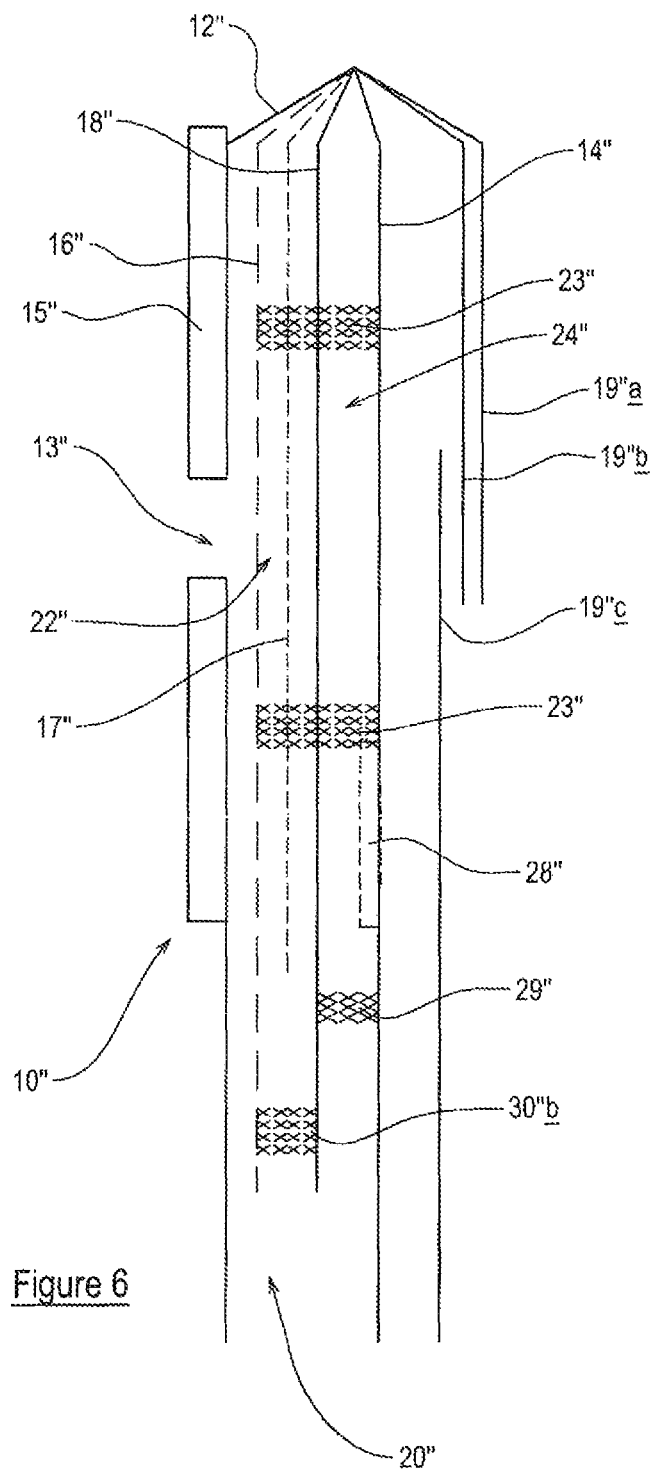
FIG. 6 is a cross-sectional view of the apparatus of FIG. 5 through the line A"

The third embodiment shown in FIGS. 5 and 6 differs from the first and second embodiments in that the fourth wall 14" is provided as a single wall along its entire length, rather than first and second portions which are connected to each other (previously by the welds 29, 29' in the first and second embodiments).

Figure 7:
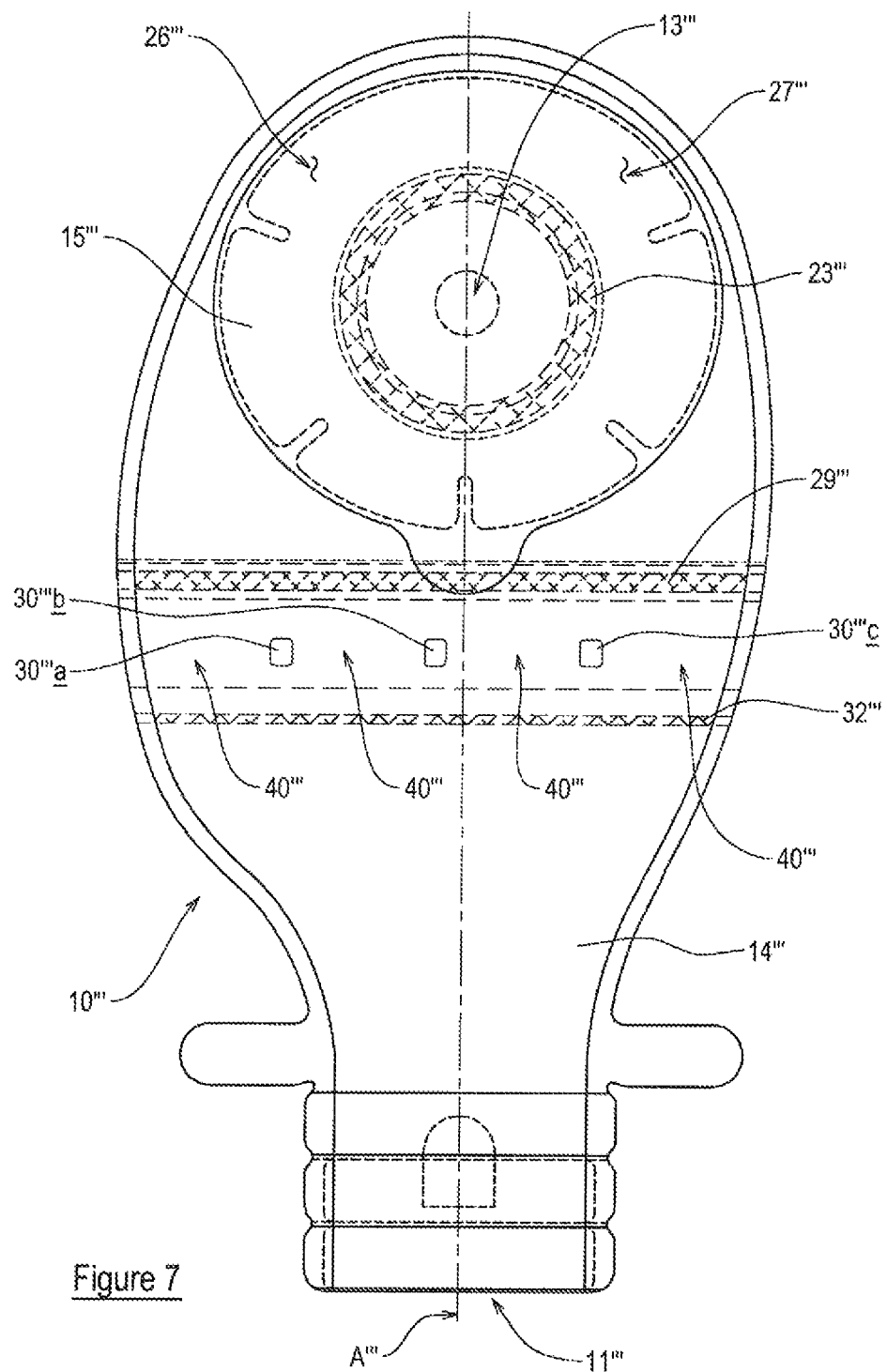
FIG. 7 is a front view of a fourth embodiment of an apparatus according to the present invention.
Figure 8:
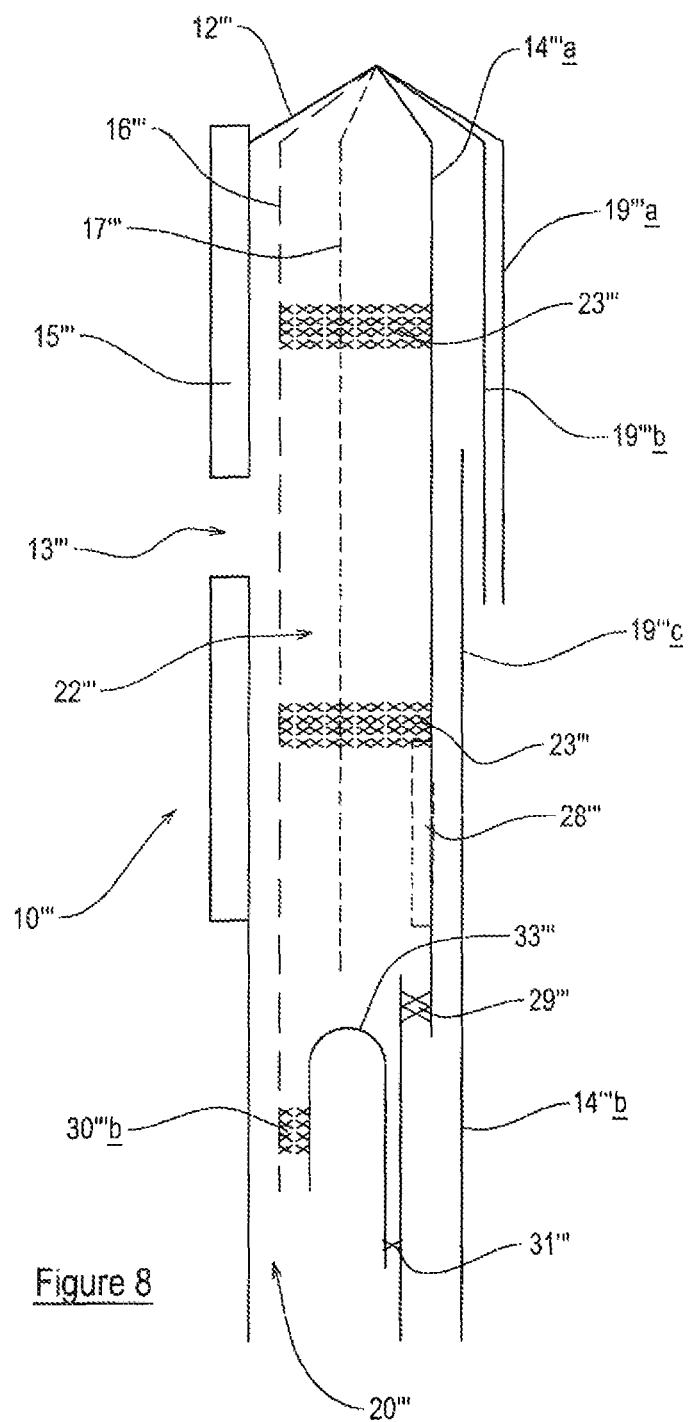
FIG. 8 is a cross-sectional view of the apparatus of FIG. 7 through the line A'.

Referring to FIGS. 7 and 8, these show a fourth embodiment of an appliance 10''' in accordance with the present invention. This embodiment is similar to the second embodiment shown in FIGS. 3 and 4, and thus like component parts/features have been given the same reference numeral with the addition of two further prime symbols. The main difference from the second embodiment is the omission of the third wall 18'. Thus, the appliance 10''' has three main walls 12''', 14''' and 16''', instead of four. The wall 14''' is split into first 14a''' and second 14b''' portions which are connected to each other along a lateral weld line 29'''. The further wall 33''' is connected along one edge 31''' to a lower most edge of the wall 14''' and its opposite edge is connected to the wall 18" by the welds 30a''', 30b''', 30c''' (which define the liquid flow paths 40'''). Again, in cross-section the wall 33''' is n-shaped in the sense that it is a single wall which is folded back on itself. This additional wall 33''' provides for increasing the available cavity space in the cavity 22''' for waste gases before they exit through the aperture 28'''.

The omission of the wall 18' means that the appliance 10''' has two interior cavities 20''', 22''', rather than the three shown in the appliance 10'. However, the appliance still works in substantially the same manner as the second embodiment, with air passing from the main cavity 20''' through the apertures 26''', 27''' and into the cavity 22'''. Air then passes from the cavity 22''' through the vent 28''' to atmosphere. Any liquid which passes through the apertures 26''', 27''' and into the cavity 22''' will advantageously flow under gravity through the flow paths 40''' back into the cavity 20'''.

It will be appreciated that any of the features of the second and third embodiment can be incorporated into the first embodiment, and vice versa, without departing with the scope of the present invention.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An ostomy appliance having:
   first and fourth walls connected to each other at or near their peripheries, the first wall having a stoma-receiving opening;
   second and third walls positioned in between the first and fourth walls;
   a waste collecting cavity defined between either the first and second walls or between the first, second and fourth walls;
   a second cavity defined between the second and third walls;
   a third cavity defined between the third and fourth walls;
   a first gas flow path in the second wall, wherein the first gas flow path permits waste gases to pass through the second wall from the waste collecting cavity to the second cavity;
   a second gas flow path in the third wall, wherein the second gas flow path permits waste gases to pass through the third wall from the second cavity to the third cavity; and
   a third gas flow path in the fourth wall, wherein the third gas flow path permits waste gases to escape through the fourth wall from the third cavity,
   wherein the second and third walls are connected to each other at their peripheries and connected to each other by at least one additional connection located at a lower portion of the second and third walls to define a liquid flow path which permits liquid within the second cavity to flow into the waste collecting cavity.

2. An appliance according to claim 1 wherein the liquid flow path permits liquid within the second cavity to flow into the waste collecting cavity under gravity.

3. An appliance according to claim 1 wherein the second and third walls are connected to each other at a connection and wherein the liquid flow path is provided as a break, gap or opening in said connection.

4. An appliance according to claim 1 wherein the first gas flow path is an aperture or slit in the second wall.

5. An appliance according to claim 1 wherein the second gas flow path is an aperture or slit in the third wall.

6. An appliance according to claim 1 wherein the third gas flow path is an aperture or slit in the fourth wall.

7. An appliance according to claim 4 wherein the aperture or slit is covered by a gas filter.

8. An appliance according to claim 1 wherein at least one of the second and third walls is smaller in surface area than the first and fourth walls.

9. An appliance according to claim 1 wherein at least one of the second and third walls is positioned towards a top of the appliance.

10. An appliance according to claim 1 wherein at least one of the second and third walls is positioned generally opposite the stoma-receiving opening in the first wall.

11. An appliance according to claim 1 wherein the appliance includes a closable outlet which communicates with the waste collecting cavity for emptying its contents.

12. An appliance according to claim 1 wherein there are two or more liquid flow paths between the second and third walls.

13. An appliance according to claim 3 wherein there are two breaks, gaps or openings in said connection of the second and third walls.

14. An appliance according to claim 11, wherein at least one of the liquid flow paths is provided in a connection of peripheral edges defined by the second and third walls which edges generally face downwardly towards the outlet.

15. An appliance according to claim 1 wherein the liquid flow path is configured to permit liquid to pass only in the direction of the second cavity to the waste collecting cavity.

16. An appliance according to claim 1 wherein the liquid flow path is a one-way valve.

17. An appliance according to claim 1 wherein the fourth wall includes first and second portions which are connected to each other.

18. An appliance according to claim 17 wherein the first and second portions of the fourth wall and the second wall are connected to each other.

19. An ostomy appliance having:—
   first and fourth walls connected to each other at or near their peripheries, the first wall having a stoma-receiving opening;
   a second wall positioned in between the first and fourth walls;
   a waste collecting cavity defined between either the first and second walls or first and fourth walls;
   a second cavity defined between the second and fourth walls;
   a first gas flow path in the second wall, wherein the first gas flow path permits waste gases to pass through the second wall from the waste collecting cavity to the second cavity; and
   a second gas flow path in the fourth wall, wherein the second gas flow path permits waste gases to escape through the fourth wall from the second cavity;
   wherein the second and fourth walls are connected to each other at their peripheries and connected to each other by at least one additional connection located at a lower portion of the second wall that defines a liquid flow path which permits liquid within the second cavity to flow into the waste collecting cavity.

* * * * *